(12) United States Patent
Harsh et al.

(10) Patent No.: US 7,652,767 B2
(45) Date of Patent: Jan. 26, 2010

(54) OPTICAL SENSOR WITH CHEMICALLY REACTIVE SURFACE

(75) Inventors: Kevin Harsh, Westminster, CO (US);
Brian Schaible, Longmont, CO (US);
Wenge Zhang, Louisville, CO (US);
William Garrett, Winston-Salem, NC (US)

(73) Assignee: Sporian Microsystems, Inc., Lafayette, CO (US)

( * ) Notice: Subject to any disclaimer, the term of this patent is extended or adjusted under 35 U.S.C. 154(b) by 0 days.

(21) Appl. No.: 11/551,158

(22) Filed: Oct. 19, 2006

(65) Prior Publication Data

US 2008/0094632 A1 Apr. 24, 2008

(51) Int. Cl.
*G01N 21/55* (2006.01)
(52) U.S. Cl. ...................................... 356/445
(58) Field of Classification Search ......... 356/445–448, 356/432–442
See application file for complete search history.

(56) References Cited

U.S. PATENT DOCUMENTS

| | | | |
|---|---|---|---|
| 5,233,194 A | 8/1993 | Mauze et al. | |
| 5,565,978 A | 10/1996 | Okubo et al. | |
| 5,570,697 A | 11/1996 | Walker et al. | |
| 5,834,777 A | 11/1998 | Wong | |
| 5,930,276 A | 7/1999 | Dou et al. | |
| 5,995,686 A | 11/1999 | Hamburger et al. | |
| 6,197,503 B1 | 3/2001 | Vo-Dinh et al. | |
| 6,379,969 B1 | 4/2002 | Mauze et al. | |
| 6,424,418 B2 | 7/2002 | Kawabata et al. | |
| 6,429,022 B1 | 8/2002 | Kunz et al. | |
| 6,465,774 B1 | 10/2002 | Walker, Jr. et al. | |
| 6,493,090 B1 | 12/2002 | Lading et al. | |
| 6,621,092 B1 | 9/2003 | Furuta et al. | |
| 6,649,357 B2 | 11/2003 | Bryan et al. | |
| 6,649,416 B1 | 11/2003 | Kauer et al. | |
| 6,738,141 B1 * | 5/2004 | Thirstrup | 356/445 |
| 7,268,864 B2 * | 9/2007 | Chiarello et al. | 356/128 |
| 2003/0076501 A1 * | 4/2003 | Hofmann | 356/445 |
| 2004/0223159 A1 * | 11/2004 | Iwata et al. | 356/445 |

OTHER PUBLICATIONS

E. Thrush, O. Levi, L.J. Cook, J. Deich, A. Kurtz, S.J. Smith, W.E. Moerner, and J.S. Harris Jr., Monolithically Integrated Semiconductor Fluorescence Sensor for Microfluidic Applications, Sensors and Actuators B, 2005, pp. 393-399, No. 105, Elsevier B.V.

J.A. Chediak, Z. Luo, J. Seo, N. Cheung, .L.P. Lee, and T.D. Sands, "Heterogeneous Integration of CdS Filters With GaN LEDs for Fluorescence Detection Microsystems," Sensors and Actuators A, 2004, pp. 1-7, No. 111, Elsevier B.V.

* cited by examiner

*Primary Examiner*—Michael P Stafira
(74) *Attorney, Agent, or Firm*—Holland & Hart LLP

(57) ABSTRACT

An improved optical sensor and methods for measuring the presence of various materials or constituents in a fluid sample uses reactive material(s) in a fluid environment. The reactive materials have optical properties that change in the presence of a target material that may be present in the environment. An optical emitter generates light that is directed to the reactive materials, and one or more optical detectors receive reflected light from one or more interfaces in the optical path between the emitter and the detector(s), one or more of the interfaces having a reactive material. The reactive material(s), emitter(s), and detector(s) are selected based on the desired target material to be sensed.

19 Claims, 8 Drawing Sheets

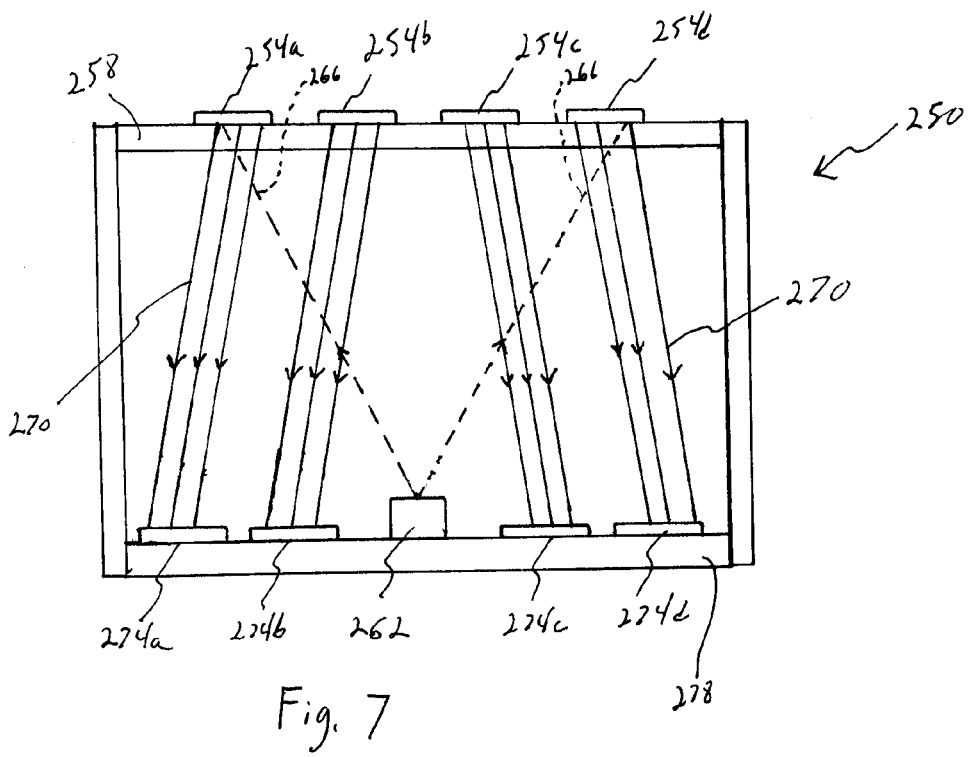
Fig. 7
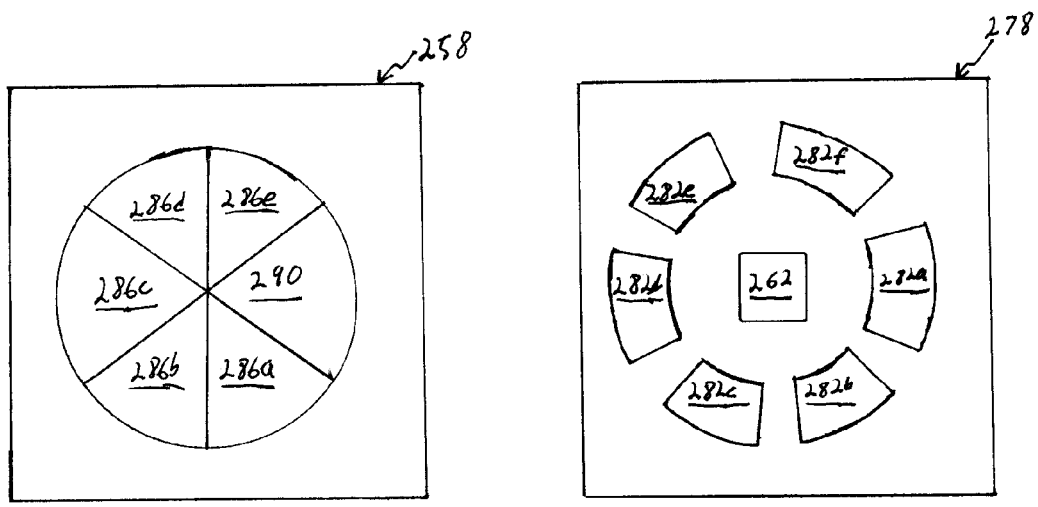
Fig. 8
Fig. 9

OPTICAL SENSOR WITH CHEMICALLY REACTIVE SURFACE

STATEMENT REGARDING FEDERALLY SPONSORED RESEARCH OR DEVELOPMENT

This invention was made with Government support under U.S. Army contract nos. DAAE30-02-C-1062, DAAE30-03-C-1075, W31P4Q-05-C-R100, and W31P4Q-06-C-0317. The Government may have certain rights to this invention.

FIELD OF THE INVENTION

The present invention generally relates to an optical sensor for sensing the presence of a chemical substance in a fluid sample. More specifically, the invention relates to measuring optical characteristics of a chemically reactive surface that is exposed to the fluid sample.

BACKGROUND OF THE INVENTION

Numerous applications require the determination of the presence or absence of one or more substances in a particular sample. In particular, several application require that the presence or absence of a material in a fluid sample be detected. Such applications include, for example, determining or monitoring of emissions from stationary or mobile sources for the presence of one or more substances in the emissions. It would be beneficial to have a sensor for detecting the presence or absence of materials in various samples that is both efficient and relatively inexpensive. Furthermore, such a sensor should be reliable and relatively fast in performing the analysis. Furthermore, many of the applications requiring such sensors are mobile or remote applications that do not have ready access to a power supply that is not a battery or other stored type of power supply. Accordingly, it would also be desirable for sensors in such applications to use relatively low power when performing analysis of the samples.

SUMMARY OF THE INVENTION

Embodiments disclosed herein address the above stated needs by providing apparatuses and methods for sensing the presence or absence of various target materials in an environment being sampled.

In one aspect an optical sensor, is provided that comprises an optical emitter mounted on a substrate; an optical detector mounted on the substrate adjacent to the optical emitter; and a reactive surface located opposite the substrate, optical emitter and optical detector. An area of the reactive surface is exposed to a fluid and an optical property of the reactive surface changes upon exposure to a target material when the target material is present in the fluid. The optical emitter emits light onto the reactive surface, and the optical detector receives reflected light from the reactive surface and detects the change in said optical property when the reactive surface is exposed to the target material. A transparent window may be located opposite the substrate, and the reactive surface located on the transparent window opposite the substrate. The optical emitter may be comprised of one or more of a vertical cavity surface emitting laser, a light emitting diode, and a laser diode. The optical emitter may also include first and second optical emitters that emit light having different optical characteristics, with a change in the reflected light optical characteristics indicating the reactive surface is exposed to the target material. The optical detector may be comprised of one or more of a photo diode, a charge coupled device, and a PIN photo detector. The optical detector may also include a first and a second optical detector, the first optical detector receiving reflected light from a first area of the reactive surface and the second optical detector receiving reflected light from a second area of the reactive surface, where the first area is not exposed to the fluid, and the second area is exposed to the fluid. The reactive surface may comprise a plurality of different reactive materials, each reactive material having an optical property that changes in a unique manner relative to other of the reactive materials when exposed to the target material.

Another aspect provides a method for determining the presence or absence of a target material in an environment, comprising the steps of (a) providing an optical sensor having an optical emitter, optical detector, and a reactive surface located in an optical path between the optical emitter and optical detector; (b) monitoring an optical characteristic of light that is reflected off of a first area of the reactive surface; (c) determining if the optical characteristic has changed, and (d) providing an indication that the target material is present in the environment when it is determined that the optical characteristic has changed. The step of monitoring, in one embodiment, comprises (i) receiving light that is reflected from a first area of the reactive surface at a first optical detector, the first optical detector generating a first output; (ii) receiving light that is reflected from a second area of the reactive surface at a second optical detector, the second optical detector generating a second output; and (iii) monitoring a ratio of the first and second outputs. The step of determining, in an embodiment, comprises (i) receiving light that is reflected from a first area of the reactive surface at a first optical detector; (ii) receiving light that is reflected from a second area of the reactive surface at a second optical detector; (iii) multiplying the first output by a scaling factor; (iv) subtracting the multiplied first output from the second output to obtain a difference output; (v) amplifying the difference output by a predetermined gain; and (vi) monitoring the amplified difference output. The scaling factor may be determined based on nominal first and second outputs so as to provide the multiplied first output that is substantially equal to the nominal second output.

In still a further aspect, an optical sensor is provided that comprises an optical emitter mounted on a substrate, an optical detector mounted on the substrate adjacent to the optical emitter, a transparent window located opposite the substrate, and a reactive surface located in the transparent window. The reactive surface has a reference surface area and a signal surface area, the reference surface area being isolated from an environment being tested and the signal surface area being exposed to the environment being tested, and an optical property of the signal surface changes upon exposure to a target material when the target material is present in the environment. The optical emitter emits light onto the signal and reference surfaces, and the optical detector receives reflected light from the signal and reference surfaces and detects the change in the optical property when the signal surface is exposed to the target material based on a difference between the reflected light from the signal and reference surfaces.

BRIEF DESCRIPTION OF THE DRAWINGS

FIG. 7 is an illustration of an embodiment of an optical sensor having multiple reactive surfaces and optical detectors;

FIG. 8 is an illustration of areas of reactive materials on a transparent window for an embodiment;

FIG. 9 is an illustration of photo detectors and an emitter on a substrate for an embodiment;

DETAILED DESCRIPTION

The present invention generally relates to an improved optical sensor and methods for measuring the presence of various materials or constituents in a fluid sample using a reactive material in the fluid sample that changes optical properties in the presence of the reactive material in the fluid sample. Optical sensors described herein use relatively little power and may also be used to sense an array of different parameters. The sensors of the various embodiments discussed herein rely on detecting a variation in intensity of light reflected onto one or more photo detectors from one or more interfaces in the optical path between an emitter and the photo detector(s). There are several general phenomena that result in intensity modulation at the photo detector(s). These phenomena in various embodiments are utilized sensor alone and/or in combination. A first general phenomena is an absorption change within the optical path, such as the amount of light absorbed by a sensitive material layer that varies due to, for example, pressure, temperature, and/or presence of a chemical, for example. As a result, the light reflected back onto the photo detector(s) from the interface changes in the presence of the desired target. A second general phenomena is an index of refraction change at one or more of the interfaces in the optical path. This phenomena results in the amount of light reflected back onto a photo detector that changes based on the index of refraction of each layer at each interface in the optical path. As the index of refraction of the sensitive material varies due to, for example, pressure, temperature, and/or presence of a chemical, the light reflected back onto the photo detector from the interfaces on either side of the sensitive material may vary. A third general phenomena is a polarization change at one or more of the interfaces in the optical path. The polarization state of the light reflected back onto the photo detector may be made to depend on the effect the various layers have on the polarization of the light from the source. Finally, a geometric change at one or more of the interfaces may alter the amount of light reflected back onto the photo detector. Such embodiments may include one or more designed features that promotes a desired deformation of some or all regions of one or more interfaces in the optical path when a force is applied (e.g. due to pressure, acceleration, temperature change, etc.) to the interface. This deformation can be designed to steer rays of light onto or off of the photo detector, thus varying the intensity of light hitting the detector. By utilizing these phenomena either singly or in combination, along with appropriate selection of sensing material(s) or appropriate design of glass features this sensing concept can be used to sense a wide range of physical and chemical parameters.

Figure 1:
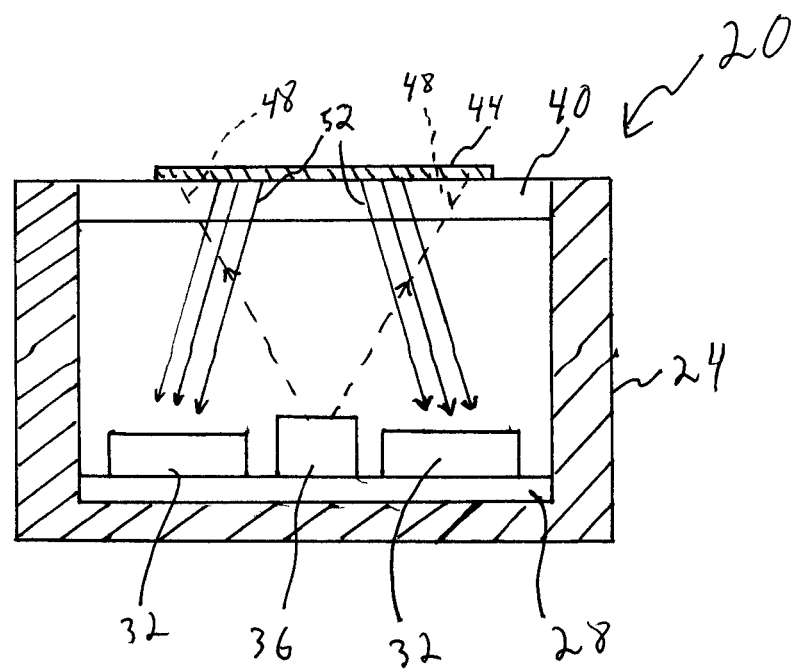
FIG. 1 is an illustration of an optical sensor of an embodiment.

With reference now to the drawing figures, various embodiments of the present invention are described. With reference to FIG. 1, an optical sensor of one embodiment is illustrated. In this embodiment, an optical sensor 20 has a housing 24 containing a substrate 28 photo detectors 32 and an emitter 36. A transparent window 40 is located opposite the substrate 28 and associated photo detectors 32 and emitter 36. A reactive surface 44 is then interconnected with the transparent window 40 on the side of the window 40 that is opposite the substrate 28 and photo detectors 32 and emitter 36. The emitter 36 emits light illustrated by dashed lines 48 in FIG. 1. The emitted light 48 strikes the reactive surface 34 which creates reflected light 52 that is reflected back towards the substrate 28. In this embodiment, photo detectors 32 are positioned to receive the reflected light. Such an optical sensor 20 may be inserted into a sample such that the reactive surface 44 comes into contact with the different constituent elements present in the sample. The reactive surface 44 is selected such that optical characteristics of the surface change in the presence of certain predetermined constituents in the sample. When the constituents are present in the sample, the reactive surface 44 changes in optical characteristics, with these changes being picked up by the photo detectors 32 monitoring the reflected light 52. The signal from the photo detectors is measured by associated circuitry which can identify the signal change from the photo detectors and provide an indication that one or more of the relevant constituents are present in the fluid stream of the optical sensor 20.

In one embodiment, the emitter 36 is a light emitting diode that emits light at a determined frequency. The light emitted from the emitter 36 illuminates or reflects off the reactive material 44, and then a portion of the emitted optical energy is cast back upon the photo detectors, which in one embodiment may be photo diodes. While described as light emitting diodes and photo diodes, it will be understood that the emitter 36 and photo detectors 32 may be any appropriate emitter, including light emitting diodes, laser diodes, vertical cavity surface emitting lasers (VCSELs), among others. Furthermore, the photo detectors may include other suitable detectors as well, such as photo diodes, charge coupled devices, PIN photo detectors, among others. Furthermore, one or more filters may be integrated into the optical sensor 20 between the emitter and/or photo detectors. Through the change of optical characteristics of the reactive material of the reactive surface 44, the intensity of the light striking the photo detectors 32 is also changed, resulting in a measurable signal change. The reactive surface 44 may undergo a chemical, physical, or other change in the presence of one or more substances that may be detected using the photo detector. The reactive surface 44 may include reactive materials that may change in one of many possible optical characteristics in the presence of certain substances, such as, for example, absorption, index of refraction, fluorescence, and photo luminescence. The material that forms the reactive surface 44 can be any of a number of different types of materials that undergo a change in the presence of one or more substances, such reactive materials may include chemically responsive thin films such as metal oxides, chemiluminecent dyes, polymer or sol gel immobilized dyes, colorimetric dyes, and/or Langmuir Blodgett films, to name a few. The reactive material may also include thermally responsive materials such as thermo-chromic dyes and polymers and dimensionally changing materials. Furthermore, the reactive surface 44 may detect physical changes such as changes in the angle of the reactive surface 44 relative to the photo detectors 32. Such a change in physical angle may be the result of, for example, expansion or contraction of the reactive surface 44 and/or one or more physical changes that result in a change of the angle at which the reactive surface 44 is situated relative to the substrate 28. Such physically responsive reactive surfaces may include structures such as mirrors, cantilevers, gratings, photoelectric materials, and others that may move, for example, by inertial forces, pressure or temperature changes, and/or induced strains.

Figure 2:
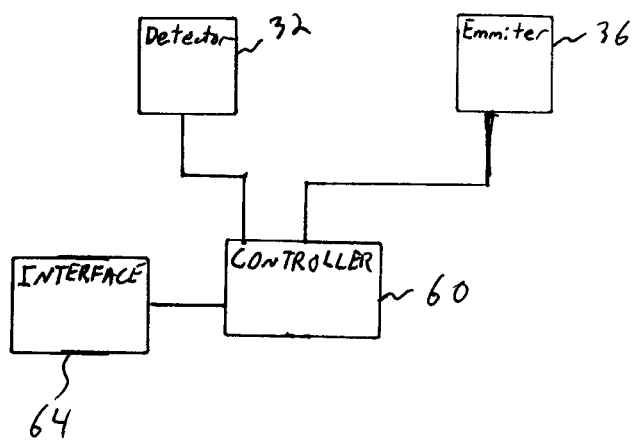
FIG. 2 is a block diagram illustration of the electronics of an optical sensor of an embodiment.

Referring now to FIG. 2, a block diagram illustrating an optical sensor of an embodiment is illustrated. In this embodiment, a controller 60 is interconnected with an emitter 36 and provides signals thereto that cause the emitter 36 to emit light. The controller is also operably interconnected with a detector portion 32, which may contain one or more photo detectors as illustrated in FIG. 1, for example. The photo detector portion 32 provides signals to the controller 60 that the controller may monitor for changes to indicate the presence of a particular substance in a sample being analyzed. The controller 60 is also interconnected with an interface 64 that may be used to provide an output indicating the signal changes received from the optical detector 32, and may provide an indication to the controller 62 provide a particular signal to the emitter 36 in order to start an analysis. The interface 64 may include a user interface including a graphical user interface, or may be an interface with another system that includes the optical detector as a component therein.

Figure 3:
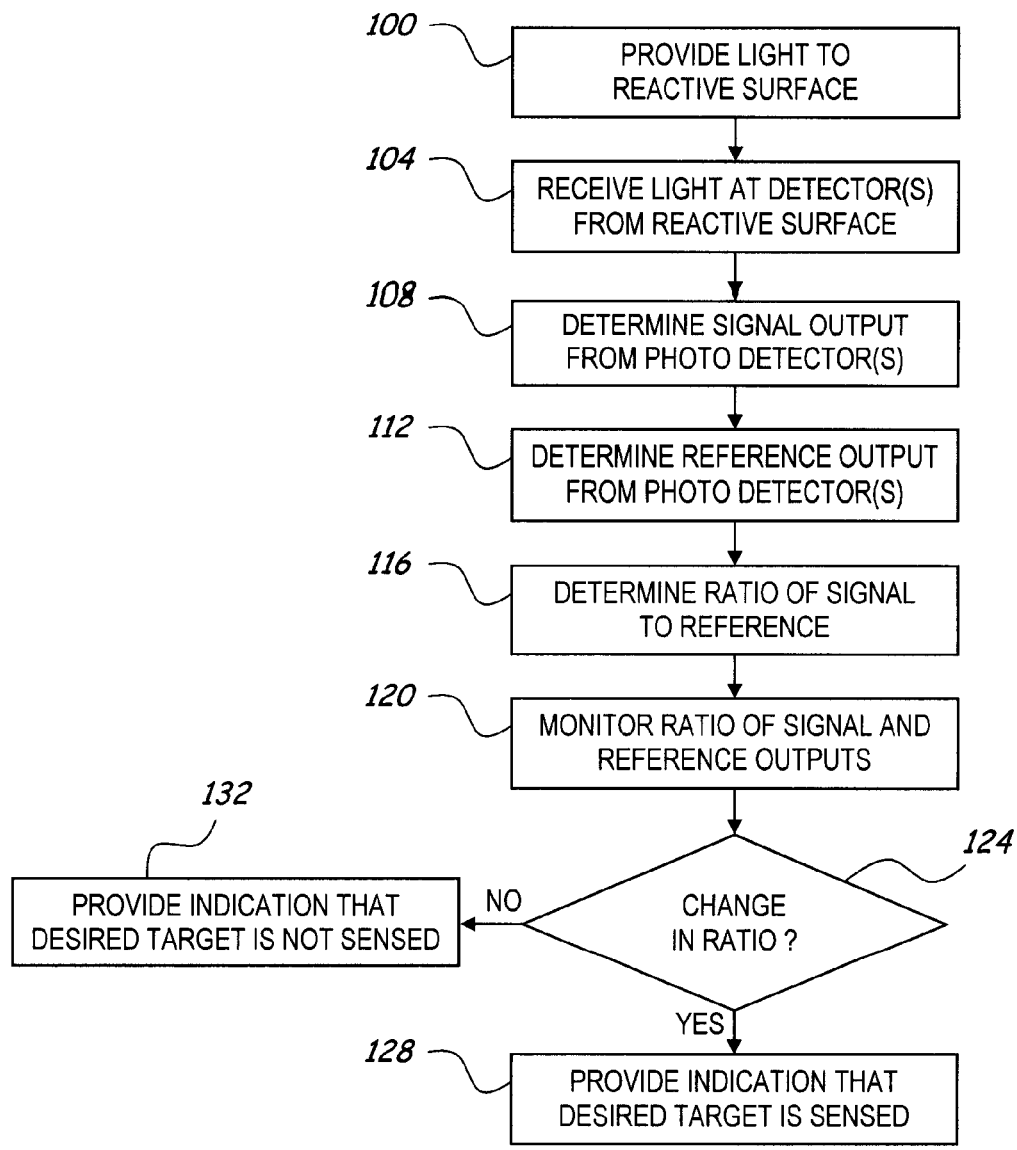
FIG. 3 is a flow chart diagram illustrating the operational steps of an optical sensor of an embodiment.

With reference to FIG. 3, a flow chart diagram illustrating the operational steps used by a photo detector of one embodiment to determine the presence or absence of a particular target material in the sample being analyzed. Initially, as indicated at block 100, the optical sensor provides light to the reactive surface associated with the optical sensor. Similarly as described with reference FIGS. 1 and 2, the optical sensor may include a photo diode or any other type of optical emitter, that provides light to a reactive surface associated with the optical sensor. At block 104, light is received from the one or more photo detectors that is reflected from the reactive surface. As described above, the photo detector may be, for example, a photo diode or multiple photo diodes. Next, at block 108, a signal output from the photo detectors is determined. At block 112, a reference output from the photo detectors is determined. In this embodiment, the reactive surface includes two different areas. A first area that is exposed to the sample being analyzed, and a second area that is not exposed to a sample being analyzed. In this embodiment, at block 108, the signal output is determined based upon the reflected light from the reactive surface that is exposed to the material being analyzed, and the reference output of block 112 is determined from the portion of the reactive surface that is not exposed to the sample being analyzed. At block 116, a ratio of the signal and reference outputs is determined. By taking a ratio of the signal to the reference, the effect of emitter intensity fluctuations that can occur as a result of power supply fluctuations, component aging, or temperature effects may be removed. In this manner, changes in the intensity of the emitter will affect the reference and signal outputs proportionally, and change in the emitter output results in the ratio remaining unchanged when the environment being sensed is constant. Thus, changes in the optically responsive sensing material(s) affect the signal output, and thus the ratio will change, indicating sensing of the desired target. Writing this embodiment as a formula, when there is a change in emitter output but the environment being sensed is constant:

$$\frac{S_{final}}{R_{final}} = \frac{S_{initial} + AS_{initial}}{R_{initial} + AR_{initial}} = \frac{S_{initial}}{R_{initial}} \qquad (1)$$

Where S is the signal output, R is the reference output, and A is the resulting change (in %) on the reference and signal outputs due to emitter output power variations. But, if the environment being sensed is changing:

$$\frac{S_{final}}{R_{final}} = \frac{S_{initial} + BS_{initial}}{R_{initial}} = \frac{(1+B)S_{initial}}{R_{initial}} \neq \frac{S_{initial}}{R_{initial}}$$

Where and B is the resulting change (in %) on the reference and signal outputs due to a change in the sensing material.

Referring again to FIG. 3, at block 120 the ratio of the signal and reference outputs is monitored, and at block 124 it is determined if there is a change in the ratio. Changes in the ratio, as mentioned, indicates that the portion of the reactive surface that is exposed to the sample being analyzed has been exposed to the desired target. At block 128, if it is determined that there has been a change in the ratio, an indication is provided that the desired target is sensed. If no change in the ratio is detected at block 124, an indication that the desired target is not sensed is provided at block 132. Furthermore, in embodiments using multiple different photo detectors, when such photo detectors have similar electrical and thermal properties, taking the ratio of the signal and reference outputs also removes proportional changes in the detectors due to power and/or temperature fluctuations. However, it will be understood that similar detectors may not always be used for various applications.

Figure 4:
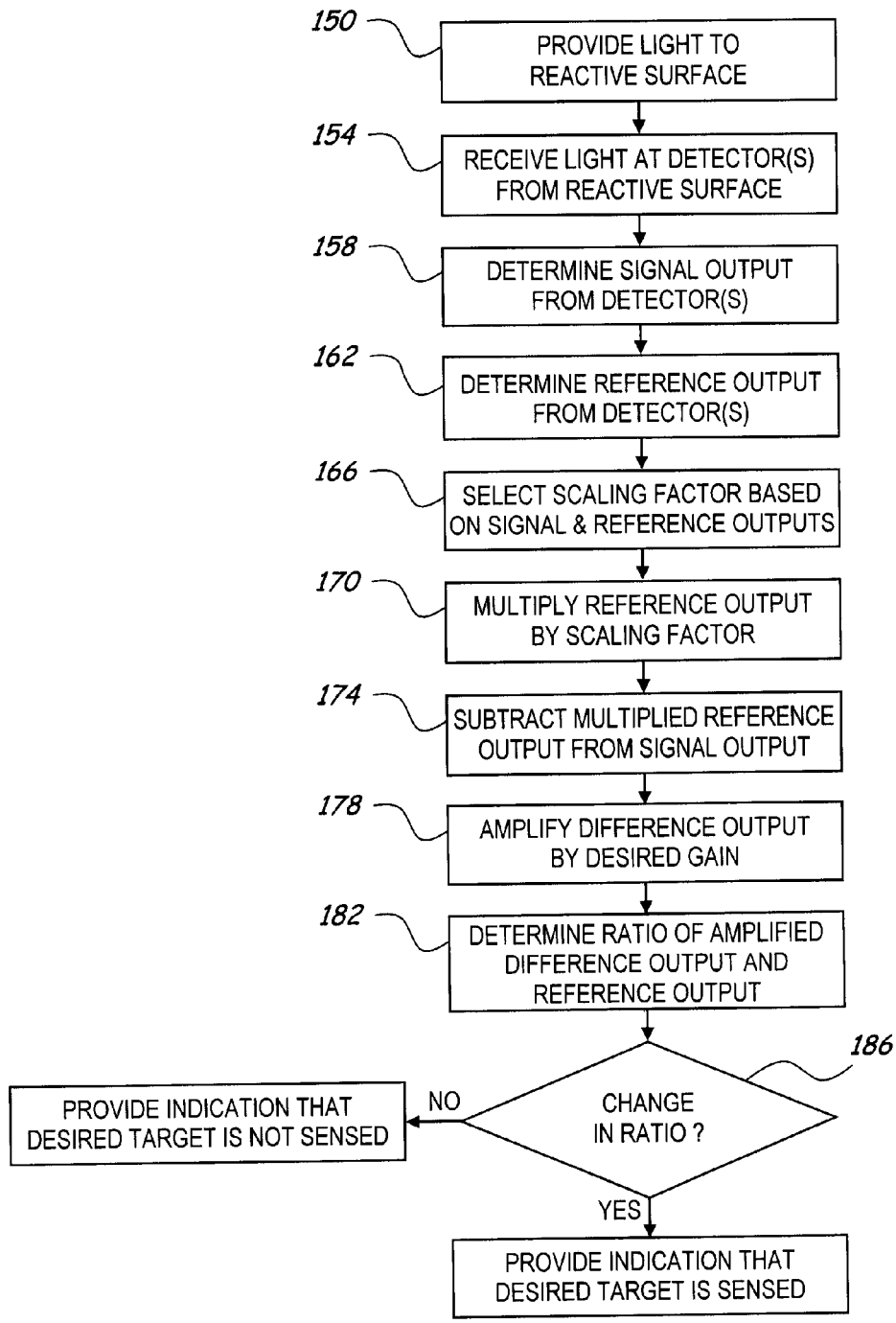
FIG. 4 is a flow chart diagram illustrating the operational steps of an optical sensor of another embodiment.

With reference now to FIG. 4, a flow chart diagram illustrating the operational steps used by a photo detector of another embodiment to determine the presence or absence of a particular target material in the sample being analyzed. Initially, as indicated at block 150, the optical sensor provides light to the reactive surface associated with the optical sensor. Similarly as described above, the optical sensor may include a photo diode or any other type of optical emitter, that provides light to a reactive surface associated with the optical sensor. At block 154, light is received at the one or more detectors that is reflected from the reactive surface. As described above, the detector may be, for example, a photo diode or multiple photo diodes. Next, at block 158, a signal output from the detector(s) is determined. At block 162, a reference output from the detector(s) is determined. In this embodiment, similar to the embodiment of FIG. 3, the reactive surface includes two different areas. A first area that is exposed to the sample being analyzed, and a second area that is not exposed to a sample being analyzed, and the signal output is determined based upon the reflected light from the reactive surface that is exposed to the material being analyzed, and the reference output is determined from the portion of the reactive surface that is not exposed to the sample being analyzed. At block 166, a scaling factor is selected based on the signal and reference outputs. The scaling factor, in an embodiment, is selected such that if the nominal reference output is multiplied by the scaling factor, the resulting multiplied reference output would be substantially equal to the nominal signal output. The signal output and the reference output may have nominal values that are different due to a variety of reasons, such as different photo detector(s) that receive the signal light and the reference light, different distances and/or angles between the signal and reference reactive surfaces and the photo detector(s), and environmental temperature differences that affect the detector and emitter operation.

At block 170, the reference output is multiplied by the scaling factor that was selected at block 166. As will be understood, the scaling factor may be greater or less than one, thus amplifying or attenuating the reference output as desired for the optical sensor. At block 174, the multiplied reference output is subtracted from the signal output, producing a difference output. In embodiments where the scaling factor is selected to produce multiplied reference output that is substantially equal to the signal output, the resulting nominal difference output is zero. Any deviations of the difference output that are then substantially different than zero may indicate that the target material is sensed. The difference output in this embodiment is then amplified by a desired gain, as indicated at block 178. The gain may be selected to produce an amplified difference output to amplify changes to the signal output that are different than any changes to the reference output, thus providing an enhanced output that may be analyzed to determine if the target material is present. At block 182, the ratio of the amplified difference output and the reference output is determined. By taking a ratio of the amplified difference output to the reference output, the effect of emitter intensity fluctuations that can occur as a result of power supply fluctuations, component aging, and/or temperature effects may be reduced or removed. Changes in the intensity of the emitter will effect the reference and signal outputs proportionally, and any change in the emitter output would then result in the ratio of the amplified difference output and the reference output remaining relatively unchanged when the environment being sensed is constant.

Again, because the reference and signal are both proportional to the emitter output, the result of this difference is also proportional to the emitter output, and thus the effects of the emitter power variation can be removed from the result similarly as described above with respect to FIG. 3. A change in the signal output only, resulting from a change in the sensing material only, can then be amplified additionally, without amplifying the offset, and still be proportional to the emitter power. When a change in the sensing material then occurs, the difference is then equal to just the amplitude of the change due to the sensing material. If this value is very small, it can then be amplified to whatever scale is desired. This final value is then divided by the reference value, to get a ratio that is unaffected by emitter power variations. Or written simply:

$$\frac{G_2(S_{initial} - G_1 R_{initial} + BS_{initial})}{R_{initial}} \Rightarrow \text{if } (S_{initial} - G_1 R_{initial} = 0) = $$

$$\frac{G_2 BS_{initial}}{R_{initial}}$$

and, when there is a change in emitter optical output:

$$\frac{G_2(AS_{initial} - G_1 AR_{initial} + BAS_{initial})}{AR_{initial}} = \frac{G_2(S_{initial} - G_1 R_{initial} + BS_{initial})}{R_{initial}}$$

Where G1 is the multiplication of the reference to equal the signal output, and G2 is any additional amplification needed to change the output scale of the signal change. This is useful for in embodiments where the change in signal is very small compared to any signal offset. Removing the offset before adding additional amplification allows for greater overall amplification and resolution of the signal output change. This calibration can be done using electronic circuit components, or computationally.

Referring again to FIG. 4, at block 186 it is determined if there is a change in the ratio. As mentioned, changes in the ratio would indicate that the portion of the reactive surface that is exposed to the sample being analyzed has been exposed to the desired target. At block 190, if it is determined that there has been a change in the ratio, an indication is provided that the desired target is sensed. If no change in the ratio is detected at block 186, an indication that the desired target is not sensed is provided at block 194. Furthermore, in embodiments using multiple different photo detectors, when such photo detectors have similar electrical and thermal properties, scaling factors for the different detectors may be selected individually to produce a nominal difference output that is zero, or close to zero. The ratio of the difference output and reference output also removes proportional changes in the detectors due to power and/or temperature fluctuations.

Figure 5:
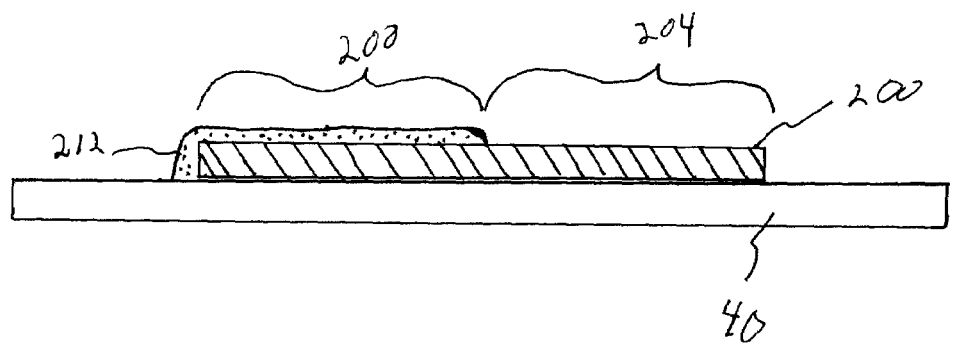
FIG. 5 is an illustration of reactive material and a transparent window of an embodiment.

As discussed above, the reactive surface is selected to react to a desired target in the sample being analyzed, and this reaction results in a change in an optical characteristic of light reflected from the reactive surface. With reference now to FIG. 5, the reactive surface 200 of one embodiment is discussed in more detail. In this embodiment, the reactive surface 200 is located on a transparent window 40 as described with respect to FIG. 1. The reactive surface 200 includes a first surface area 204 that is exposed to the surrounding environment, and a second area 208 that is not exposed to the outside environment. In this embodiment, the second surface area 208 is encapsulated by an epoxy 212 such that the reactive material of the second surface area 208 is insulated from the surrounding environment. As will be understood, numerous other types of materials and configurations may be used to insulate the second surface area 208 from the sample being tested, so long as the insulating material provides an adequate barrier between the sample being tested and the second surface area 208. For example, the second surface area 208 may be coated with a metal, metal oxide, sol gel derived material, glass material, as well as one or more types of polymer with insulative properties, to name but a few. Furthermore, some embodiments do not have a reactive surface with two separate surface areas, instead having only a single area with a reactive surface that covers a portion of the transparent window. Light reflected from this portion of the transparent window may then be compared to reflected light from portions of the transparent window that do not have the reactive material. In the embodiment of FIG. 5, the reactive surface 200 is relatively thin, such that exposure to the desired target to the first surface area 204 will result in light reflected off of the opposite side of the reactive surface will have a changed optical property. The thickness of the reactive surface 200 is thus dependent upon the material of the reactive surface, and the desired target. Reactive materials for the reactive surface 200 are generally unique materials that exhibit a chemical reaction when in contact with the desired target. Such reactive materials include metal oxides with an index of refraction that exhibits a change in response to exposure to certain chemicals. For example, a 2000 nm film of $BaTiO_3$ will change index detectably in response to humidity. Other example metal oxides that may be similarly used include, but are not limited to: $WO_3$, $SnO_2$, $In_2O_3$, and $Al_2O_3$.

Figure 6:
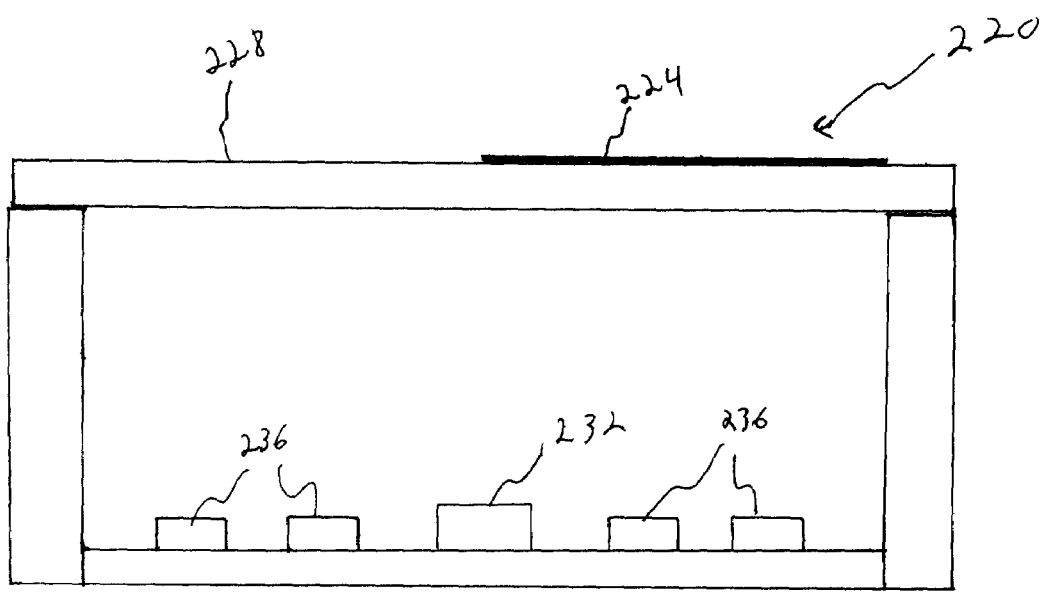
FIG. 6 is an illustration of an embodiment of an optical sensor and reactive surface on a portion of a transparent window.

FIG. 6 is an illustration of an optical detector 220 having a 2000 nm film of $BaTiO_3$ metal oxide as a reactive surface 224. The reactive surface 224 is deposited on a portion of transparent window 228. The emitter and detector hardware, in this embodiment, include an 850 nm VCSEL emitter 232, and several silicon based photo detectors 236. In the event that the reactive surface 224 is exposed to the desired target, the desired target, in this embodiment, humidity (i.e. water molecules), reacts with the $BaTiO_3$ and changes the reactive surface 224 in both the intensity of the light reflected (index of refraction) and the direction of the light reflected (angle of reflection). The position and shape of the detectors 236 is determined based on the different optical characteristics of the reflected light when the reactive surface 224 is exposed to the desired target and when the reactive surface 224 is not exposed to the desired target. The detectors 236, in this embodiment, are placed such that the reflected light position change maximizes the change in total intensity on the detectors. If a region of the sensor window is left bare (without any oxide coating), as in FIG. 6, the light reflecting from that region will not change in response to humidity, and will be proportional to the emitter 232 output intensity, thus acting as a power reference. In other embodiments, the detectors are positioned appropriately such that multiple oxides can be used to sense multiple chemicals, with the same sensor target. Other metal oxides that may be similarly used include, for example, $WO_3$, $SnO_2$, $In_2O_3$, and $Al_2O_3$.

While a metal oxide is illustrated in FIG. 6 as the reactive surface 224, various other materials may also be used. For example, certain embodiments utilize polymers with entrapped dyes exhibiting a colorimetric change. More specifically, certain dyes, immobilized in certain polymers will exhibit a colorimetric change in response to exposure to certain chemicals. For example, the dye crystal violet, immobilized in the proton exchange polymer Nafion will exhibit a color shift from yellow to blue when exposed to humidity. The emitter and detector hardware used in such an embodiment may be a LED emitting at 600 nm, and multiple silicon photo detectors. In the presence of humidity (water molecules) the polymer and dye will absorb the 600 nm light, and decrease the optical signal hitting the detectors. Again, the position of the detectors is determined such that the reflected light maximizes the change in total intensity on the detectors. Other dyes immobilized in polymers that may be similarly used include, for example, methylene blue in polymethyl methacrylate (PMMA), methylene green in gelatin, and CoCl in polyvinyl alcohol (PVA).

In addition to composition of the reactive material, hardware features may also be modified and selected based on the desired target for the optical sensor. More specifically, The type of emitter may be selected based on properties of the reactive surface and the desired target. Emission wavelength, for example, may be selected to provide an enhanced change in the light at the specified wavelength in the presence of the desired target. Similarly, emitter type may be selected to provide enhanced light change from the reactive surface. Additionally, an optical sensor may include one or more different emitter types based on properties of the reactive surface(s) and the desired target(s). Such emitter types may include, for example, LED, RCLED, edge emitting laser diode, and VCSEL. Furthermore, the type of detector may be selected to detect expected changes in the reflected light in the presence of the desired target, and one or more different types of detectors may be used in a sensor. Such detectors may include, for example, silicon based photo detectors, a CCD or CCD array, photodiodes, photoresistors, phototransistors, thermal detectors (bolometers), 1D or 2D arrays, compound semiconductor-based photodetectors, and metal-semiconductor-metal (MSM) detectors. In still further embodiments, the optical sensor includes dielectric or absorptive filters to enhance changes in the reflected light. The distance of the reactive material from the detectors may also be selected based on the characteristics of the light reflected from the reactive surface in the presence and absence of the desired target. The material of the transparent window may also be selected to provide enhanced detection of the desired target, and/or the reactive material may be placed only in certain regions on the window. In even further embodiments, reflectors and/or mirrors are included in the optical sensor that direct light to detectors. Some examples of such embodiments will be described in further detail below.

While the embodiments of FIGS. 1-6 describe an optical sensor designed with a single reactive material on the sensor window to detect the concentration or the presence/absence of a single material in the environment, such as a chemical vapor or relative humidity, other embodiments are capable of detecting the presence/absence of more than one target material in the environment. Furthermore, in many applications, the reactive surface may react to the target material, as well as other materials that are not of interest. For example SnO is an oxide material that reacts to many airborne materials including relative humidity, temperature, the vapors of a number of volatile organic compounds, and many other chemicals. Thus, a reactive surface having material based on SnO will react to all of these different materials in the environment, and generate a signal. However, in such a case, there is no way to determine if the sensor was exposed to, for example, water vapor or methanol vapor. In one embodiment, illustrated in FIG. 7, additional reactive surface regions may be included in a sensor 250, with different regions having different reactive materials. In this embodiment, several different reactive surfaces 254a, 254b, 254c, 254d, are located on the transparent window 258. Similarly as described above, the reactive surfaces 254a-d, are placed on the transparent window 258 so as to be exposed to an environment where it is desired to determine of one or more target materials are present. In this embodiment, the optical sensor 250 includes an optical emitter 262, that may be any appropriate optical emitter such as described above. Emitted light 266 from the optical emitter 262 reflects off of the reactive surfaces 254, and the reflected light 270 is received at an array of optical detectors 274a, 274b, 274c, and 274d. The emitter 262 and photo detectors 274 are mounted on a substrate 278. In this embodiment, the reactive materials 254a-d are placed on the transparent window 258 such that reflected light 270 from the reactive surfaces 254a-d is directed to respective photo detectors 274a-d. In one embodiment, one of the reactive surfaces 254, such as reactive surface 254d, is a reference surface, and thus the output from the associated photo detector 274d is used as the reference output, with the outputs from each of the remaining photo detectors 274a, 274b, and 274c, being signal outputs. When one or more reactive materials 254a-c exhibit a response to materials in the environment of the sensor, these reactions differ based on the presence/absence of different materials in the environment, and it is possible to use the electrical signal from the respective reactive material and photo detector pairs as inputs to a pattern recognition algorithm. If the pattern recognition algorithm is properly defined based on known responses, the overall sensor system can be made to distinguish different chemicals or other inputs even if each individual reactive material/photo detector pair cannot be used to make such a determination.

While the embodiment illustrated in FIG. 7 has four regions that are monitored, FIGS. 8-9 illustrate another embodiment in which a sensor has six photo detector regions 282a-f on the substrate 278, five reactive material regions 286a-e on the transparent window 258, and one reference material region 290 on the transparent window 258. While the embodiment of FIGS. 7-9 include a reference material and associated photo detector for the reference material that provides a reference output for power and temperature compensation purposes, other embodiments do not have such reference elements because power and temperature compensation is not necessary for using pattern recognition to detect the presence/absence of target materials in the environment.

Referring still to FIGS. 8-9, photo detector regions 282b through 282f produce variable photocurrents that depend on the makeup of the environment surrounding the reactive material regions 286a-e at a given time. These photocurrents can be adjusted to compensate for temperature and power variations with the photocurrent generated by the reference detector 282a to yield compensated outputs for each reactive material regions 286a-e. The five reactive material regions 286a-e are occupied by five different reactive materials that all respond to, and respond differently to, for example, four different chemicals of interest. The precise state of the reactive materials 286, and thus the five different photocurrents, in depend on the concentrations, CA, CB, CC, and CD, of the four chemicals of interest. It should be noted that the values for the number of photodetectors, reactive material regions, and chemicals of interest here are used only as an example for purposes of discussion, and the numbers needed for particular applications may vary. By exposing the reactive material regions 286 to various controlled concentrations of the four chemicals and recording the compensated outputs of the photo detectors 282b-f for each known environmental condition, training data for training the pattern recognition algorithm are obtained. The training data set consists of a suitably sufficient number of input/output groups that can describe the nature of the behavior of the optical sensor when exposed to the various combinations of chemicals of interest. In order to reduce the need for a human to define the nature of this relationship, various embodiments rely on a properly trained pattern recognition algorithm to predict the concentrations of the chemicals of interest based on the amplitudes of the electrical signals produced by the photo detectors 282a-f. A variety of pattern recognition algorithms can potentially be used with an optical sensor of the type described here. Examples include neural networks, fuzzy logic models, and hidden Markov models. In each case, the pattern recognition algorithm is treated as a "black box" mathematical model with a suitably large number of adjustable parameters. These adjustable parameters are adjusted through a "training" process that is typically unique to the particular pattern recognition algorithm being used until, when the algorithm is given inputs, which correspond to the outputs of the photo detectors the outputs of the model predict the concentrations of the chemicals of interest to a suitable level of accuracy.

Figure 10:
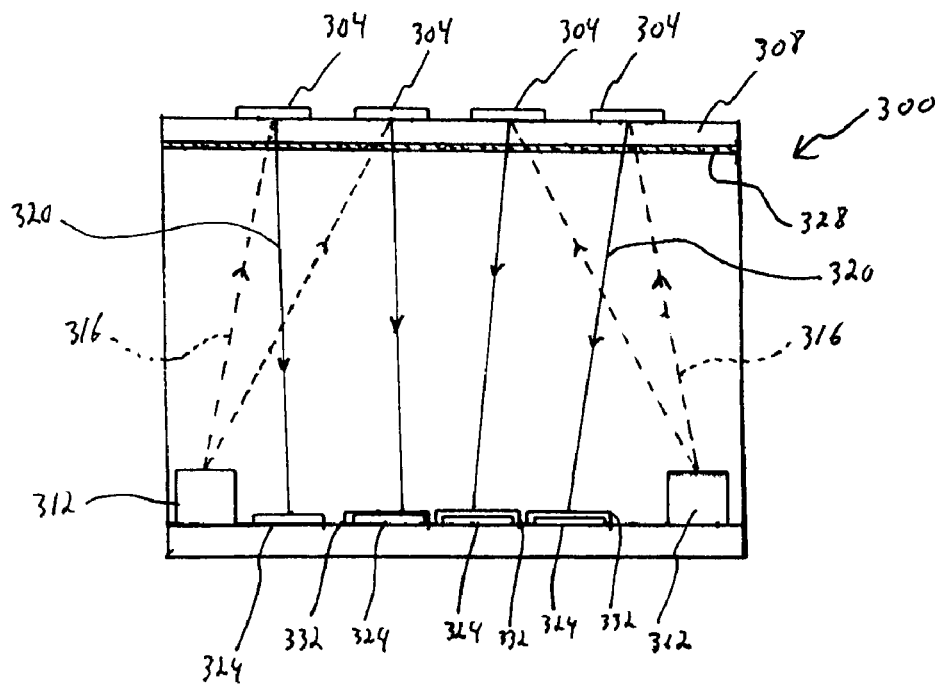
FIG. 10 is an illustration of an optical sensor and associated filters for an embodiment.

Referring now to FIG. 10, an embodiment is illustrated that utilizes multiple optical sources and filters. In this embodiment, an optical sensor 300 includes a number of reactive surfaces 304 that are located on a transparent window 308. In this embodiment, multiple emitters 312 are used to generate light 316 that is directed to the reactive surfaces 304. The multiple emitters 312 may generate light having different wavelengths, and one or more of the reactive surfaces may be selected such that the change in optical properties of the reflected light is relatively sensitive to the wavelength associated with the particular emitter. Similarly, the different emitters may produce light with other differing properties, such as different polarizations, different angles relative to the reactive surfaces, and/or different intensity, to name but a few. The light 316 reflects off of the reactive surfaces 304 and the reflected light 320 is directed to multiple photo detectors 324. Additionally, in this embodiment, the optical sensor 300 includes several filters and/or coatings that are associated with different components. In the embodiment of FIG. 10, an anti-reflective coating 328 is located on the transparent window 308. Such anti-reflective coatings 328 are well known in optics and optical systems, and serves to reduce the reflection that is generates from the surface of the transparent window 308 that is opposite the reactive surfaces 304, thus reducing the noise that may be present from the photo detectors 324 that may result from light reflected from the lower surface of the transparent window 308. Furthermore, in the embodiment illustrated in FIG. 10, several of the photo detectors also include thin film and/or absorption filters 332. Such filters may further enhance the signal output from the photo detectors 324. Such filters 332 may include, for example, polymer films such as PMMA or polystyrene-co-methyl cethaerylate (PSMMA) doped with specific wavelength absorbing dyes or pigments, glasses doped with specific wavelength absorbing dyes or pigments, controlled thickness dielectric films, and solid films made from materials with specialized absorption characteristics.

Figure 11:
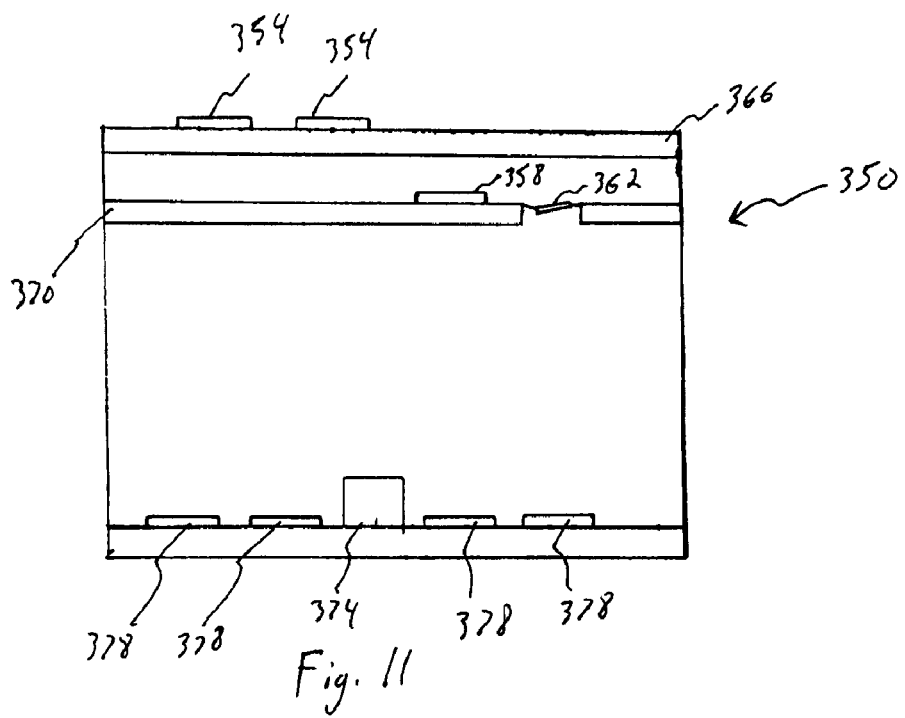
FIG. 11 is an illustration of an optical sensor having multiple reactive surfaces and transparent windows for an embodiment.

Referring now to FIG. 11, an illustration of another embodiment is illustrated. In this embodiment, an optical sensor 350 includes reactive surfaces 354 similar to the reactive surfaces previously described, and also includes a reactive surface 358 and a physical surface 362. Light emitted from an emitter 374 reflects off of the reactive surfaces 354, 358, 362, and is received at optical detectors 378. In this embodiment, a first transparent window 366 has the reactive surfaces 354, and a second transparent window 370 has the reactive surfaces 358, 362. In this manner, the reactive surfaces 358, 362, may be protected from the environment external to the first transparent window 370. For example, the reactive surface 358 may be responsive to temperature differences, and the reactive surface 362 may be an inertial responsive sensing area, both of which do not require exposure to function, and thus are protected from the environment. Conversely, the chemically and/or biologically sensitive areas 354 are exposed to the environment, without compromising the function of the optical sensor 350.

Figure 12:
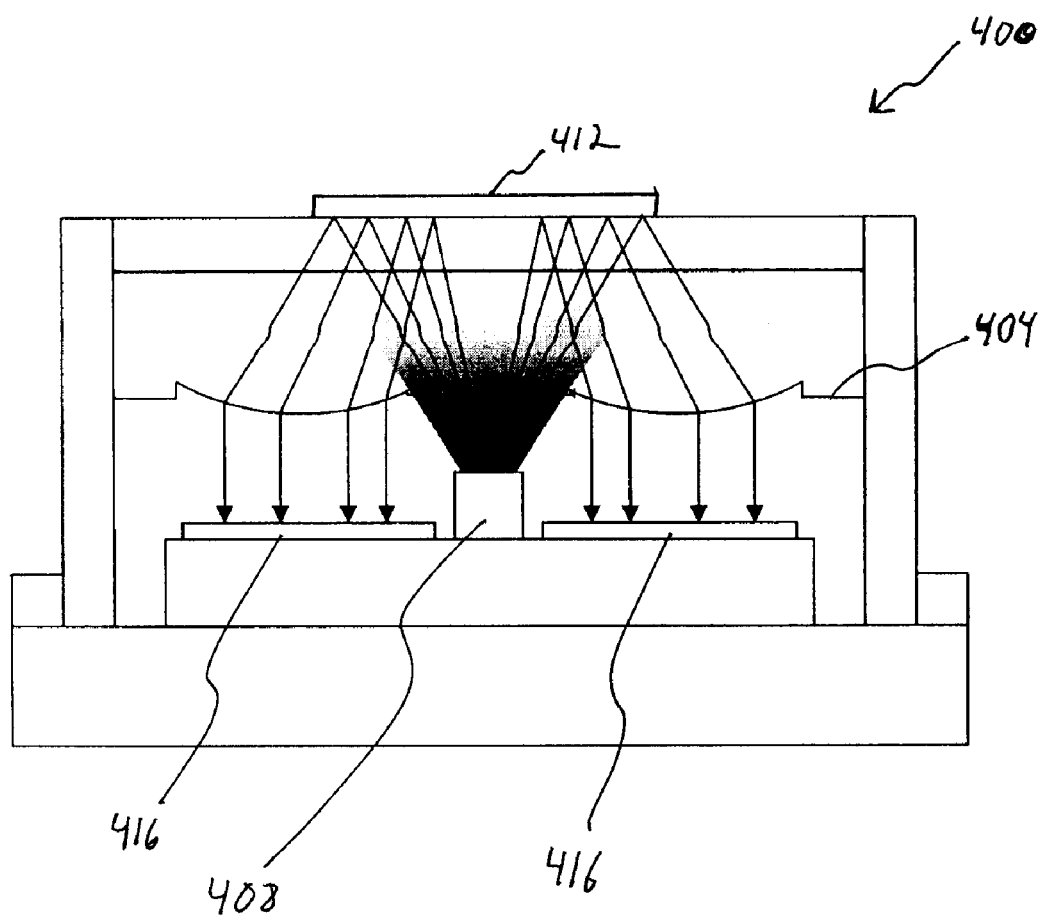
FIG. 12 is an illustration of an optical sensor having a lens shaped window for an embodiment.

FIG. 12 illustrates a further embodiment in which an optical sensor 400 includes a lens shaped window 404. In this embodiment, light emitted from an emitter 408 reflects off of the reactive surface 412, and travels through lens shaped window 404 before being received at optical detectors 416. In this embodiment, the lens shaped window 404 guides the reflected light to the optical detectors 416 in order to focus or otherwise direct the light to the detectors 416 in a manner that may be optimal for a particular application.

Figure 13:
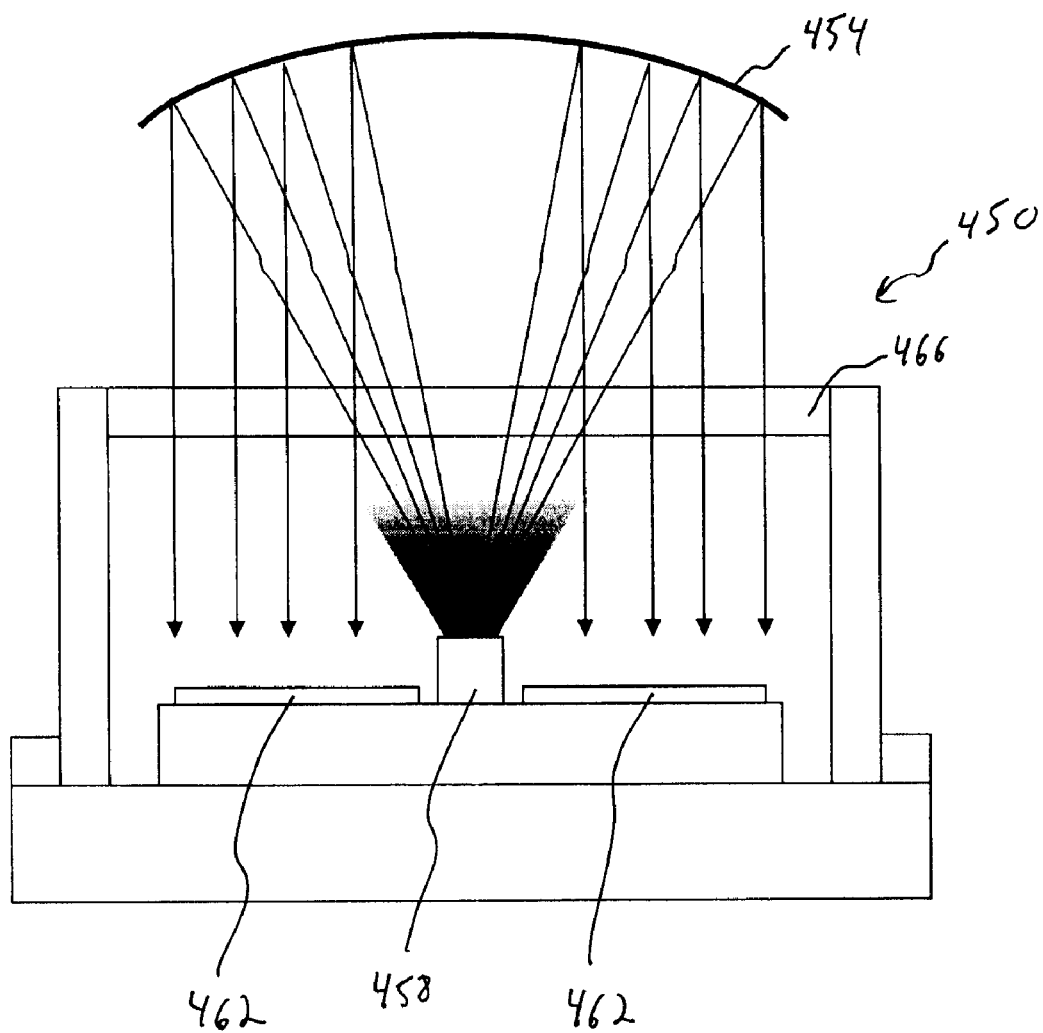
FIG. 13 is an illustration of an optical sensor having a shaped reflector for an embodiment.

FIG. 13 illustrates another embodiment in which light may be guided to provide an appropriate amount of light at the optical detectors. In the embodiment of FIG. 13, an optical sensor 450 includes a shaped reflector 454 that reflects light from an emitter 458 to optical detectors 462. A reactive surface may be included on the shaped reflector 454 such that a change in the optical properties of the reflected light may be used to detect the presence or absence of one or more target materials in the environment being sampled. The embodiment of FIG. 13 may also include a reactive surface on window 466, with the reactive surface being transparent at the wavelength of the optical emitter and/or the wavelength of a changed optical signal that may result from the presence of one or more target materials in the environment being sampled.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An optical sensor, comprising:
   an optical emitter mounted on a substrate;
   an optical detector mounted on said substrate adjacent to said optical emitter; and
   a reactive surface located opposite said substrate, optical emitter and optical detector, wherein an area of said reactive surface is exposed to a fluid and an optical property of said reactive surface changes upon exposure to a target material,
   wherein said optical emitter emits light onto said reactive surface, and said optical detector receives reflected light from said reactive surface and is operable to detect the change in said optical property when said reactive surface is exposed to said target material, the change in optical property being independent of an angle of incidence of said emitted light onto said reactive surface and including at least one of a change in index of refraction, a change in optical absorption, a change in polarization of the reflected light, a change in fluorescence, and a changed optical property resulting from a change in geometry of said reactive surface, and
   wherein said optical detector comprises a first and a second optical detector, said first optical detector located on said substrate to receive reflected light from a first area of said reactive surface and said second optical detector located on said substrate to receive reflected light from a second area of said reactive surface that is different than said first area.

2. The optical sensor, as claimed in claim 1, further comprising:
   a transparent window located opposite said substrate, and wherein said reactive surface is located on said transparent window on a side of said transparent window that is opposite said substrate, and wherein said optical emitter emits light that travels through said transparent window, reflects off of said reactive surface, travels back through said transparent window, and the reflected light is received at said optical detector.

3. The optical sensor, as claimed in claim 2, further comprising:
   an anti-reflective coating located on the side of said transparent window that is towards said substrate.

4. The optical sensor, as claimed in 1 wherein said optical emitter is comprised of at least one of a vertical cavity surface emitting laser, a light emitting diode, and a laser diode.

5. The optical sensor, as claimed in claim 1, wherein said optical emitter comprises a first and a second optical emitter, said first optical emitter emitting light having a first optical characteristic, and said second optical emitter emitting light having a second optical characteristic that is different than said first optical characteristic.

6. The optical sensor, as claimed in claim 5, wherein said first and second optical characteristics are selected from the group consisting of wavelength, polarization, and intensity.

7. The optical sensor, as claimed in claim 1, wherein said optical detector is comprised of at least one of a photo diode, a charge coupled device, and a PIN photo detector.

8. The optical sensor, as claimed in claim 1, wherein said first area of said reactive surface is not exposed to said fluid, and said second area of said reactive surface is exposed to said fluid.

9. An optical sensor, comprising:
   an optical emitter mounted on a substrate;
   an optical detector mounted on said substrate adjacent to said optical emitter; and
   a reactive surface located opposite said substrate, optical emitter and optical detector, wherein an area of said reactive surface is exposed to a fluid and an optical property of said reactive surface changes upon exposure to a target material when said target material is present in said fluid, and
   wherein said optical emitter emits light onto said reactive surface, and said optical detector receives reflected light from said reactive surface and is operable to detect the change in said optical property when said reactive surface is exposed to said target material;
   wherein said optical detector comprises a first and a second optical detector, said first optical detector located on said substrate to receive reflected light from a first area of said reactive surface and said second optical detector located on said substrate to receive reflected light from a second area of said reactive surface that is different then said first area;
   wherein said first area of said reactive surface is not exposed to said fluid, and said second area of said reactive surface is exposed to said fluid; and
   wherein said first optical detector generates a reference output, and said second optical detector generates a signal output, and a ratio of said reference and signal outputs is used to determine the presence or absence of said target material.

10. The optical sensor, as claimed in claim 1, wherein said reactive surface comprises a plurality of different reactive materials, each of said reactive materials having an optical property that changes in a unique manner relative to other of said reactive materials when exposed to said target material.

11. The optical sensor, as claimed in claim 1, further comprising at least one optical filter located in an optical path between said optical emitter and said optical detector.

12. A method for determining the presence or absence of a target material in an environment, comprising:
   providing an optical sensor having an optical emitter, optical detector, and a reactive surface located in an optical path between said optical emitter and optical detector;
   monitoring an optical characteristic of light that is reflected off of a first area of said reactive surface;
   determining if said optical characteristic has changed, the change in optical characteristic being independent of an angle of incidence of said emitted light onto said reactive surface and including at least one of a change in index of refraction, a change in optical absorption, a change in polarization of the reflected light, a change in fluorescence, and a changed optical property resulting from a change in geometry of said reactive surface, and
   providing an indication that said target material is present in the environment when it is determined that said optical characteristic has changed, wherein said step of monitoring comprises:

receiving light from a first area of said reactive surface at a first optical detector, said first optical detector generating a first output based on the light received at the first optical detector;

receiving light from a second area of said reactive surface at a second optical detector, said second optical detector generating a second output based on the light received at the second optical detector; and monitoring a ratio of said first and second outputs.

13. A method for determining the presence or absence of a target material in an environment, comprising:

providing an optical sensor having an optical emitter, optical detector, and a reactive surface located in an optical path between said optical emitter and optical detector;

monitoring an optical characteristic of light that is reflected off of a first area of said reactive surface;

determining if said optical characteristic has changed, and providing an indication that said target material is present in the environment when it is determined that said optical characteristic has changed;

wherein said step of determining comprises:

receiving light that is reflected from a first area of said reactive surface at a first optical detector, said first optical detector generating a first output based on the light received at the first optical detector;

receiving light that is reflected from a second area of said reactive surface at a second optical detector, said second optical detector generating a second output based on the light received at the second optical detector; and multiplying said first output by a scaling factor;

subtracting said multiplied first output from said second output to obtain a difference output;

amplifying said difference output by a predetermined gain; and monitoring said amplified difference output.

14. The method, as claimed in claim 13, wherein said scaling factor is determined based on nominal first and second outputs so as to provide said multiplied first output that is substantially equal to said nominal second output.

15. An optical sensor, comprising:

an optical emitter mounted on a substrate;

an optical detector mounted on said substrate adjacent to said optical emitter;

a transparent window located opposite said substrate; and a reactive surface located on said transparent window on a side of said transparent window that is away from said substrate, said reactive surface having a reference surface area and a signal surface area, said reference surface area being isolated from an environment being tested and said signal surface area being exposed to the environment being tested, wherein an optical property of said signal surface changes upon exposure to a target material when said target material is present in the environment, and wherein said optical emitter emits light onto said signal and reference surfaces, and said optical detector receives reflected light from said signal and reference surfaces and is operable to detect the change in said optical property when said signal surface is exposed to said target material based on a difference between the reflected light from the signal and reference surfaces.

16. The optical sensor, as claimed in claim 15, wherein said optical detector comprises a first and a second optical detector, said first optical detector located on said substrate to receive reflected light from said signal surface area and said second optical detector located on said substrate to receive reflected light from said reference surface area.

17. The optical sensor, as claimed in claim 15, wherein said reactive surface comprises a plurality of different reactive materials, each of said reactive materials having an optical property that changes in a unique manner relative to other of said reactive materials when exposed to said target material.

18. The optical sensor, as claimed in claim 15, further comprising at least one optical filter located in an optical path between said optical emitter and said optical detector.

19. The optical sensor, as claimed in claim 1, wherein said first optical detector generates a reference output, and said second optical detector generates a signal output, and a ratio of said reference and signal outputs is used to detennine the presence or absence of said target material.

* * * * *